United States Patent [19]

Barstow et al.

[11] Patent Number: 5,064,940

[45] Date of Patent: Nov. 12, 1991

[54] PREMIXED DRY REAGENT CONTAINING A PROTECTED AMINO ACID AND AN ACTIVATING AGENT FOR USE IN SOLID PHASE PROTEIN SYNTHESIS

[75] Inventors: Leon E. Barstow; Glen D. Ward, both of Tucson, Ariz.

[73] Assignee: Protein Technologies, Inc., Tuscon, Ariz.

[21] Appl. No.: 582,828

[22] Filed: Sep. 14, 1990

Related U.S. Application Data

[63] Continuation of Ser. No. 192,837, May 11, 1988, abandoned.

[51] Int. Cl.$^5$ .............................. C07K 1/06; C07K 1/00
[52] U.S. Cl. .................................... 530/334; 530/333; 530/335
[58] Field of Search .................. 530/334, 333, 335; 514/93

[56] References Cited

U.S. PATENT DOCUMENTS 4,888,385  12/1989  Hudson ................................ 530/334
4,965,343  10/1990  Felix et al. ........................... 530/334

OTHER PUBLICATIONS

Nguyen and Castro, Peptide Chemistry 1987: T. Shiba & S. Sakakibara (ed.), 1988.
Bodanszky, *Principles of Peptide Synthesis*, Springer-Verlag, 1984, pp. 238-239.
D. Hudson, J. Org. Chem. 53, 617-624 (1988).

*Primary Examiner*—Howard E. Schain
*Assistant Examiner*—Susan M. Perkins
*Attorney, Agent, or Firm*—Kenyon & Kenyon

[57] ABSTRACT

A novel and convenient process is described for providing protected amino acids and activating agents for solid phase synthesis which drastically reduces the capital costs of equipment required for the preparation of peptides. The two normally very reactive reagents, when mixed as anhydrous powders are shelf stable and yet form an active compound rapidly when mixed together in solution. This invention presents a method for combining these highly reactive dry solids in a manner which makes them unreactive and shelf stable at room temperature for extended periods of time. Once the solids are dissolved in solvent, a highly reactive amino acid ester that can readily be used in solid phase peptide synthesis is formed. This method of delivery of reagents to an automated peptide synthesizer allowers a very simplified instrument to be constructed using fewer and less expensive components and significantly reducing the associated software required.

10 Claims, No Drawings

PREMIXED DRY REAGENT CONTAINING A PROTECTED AMINO ACID AND AN ACTIVATING AGENT FOR USE IN SOLID PHASE PROTEIN SYNTHESIS

This application is a continuation of application Ser. No. 192,837, filed May 11, 1988, now abandoned.

This invention relates to a novel chemical reagent for peptide synthesis, and to a simplified peptide synthesis using the reagent. More particularly, this invention relates to a two-component reagent useful in solid phase peptide synthesis, which allows greatly simplified procedures for effecting peptide synthesis, and to the resulting improved synthesis.

BACKGROUND OF THE INVENTION

Many amino acids occur in nature and are characterized by having at least one carboxyl group and one amino group separated by one or more carbons. Peptides are condensation products resulting from elimination of water between the carboxyl group of one amino acid and the amino group of another. In addition, other reactive groups may be present in the individual amino acids.

Because of the extraordinary high unit value of some peptides, such as peptide hormones and peptide vaccines, this area of chemistry has received a great deal of attention. Some synthetic peptides, such as reaction catalysts and food additives like the artificial sweetener, Aspartame, have also become important industrial specialty chemicals.

The chemical preparation of a peptide is accomplished either by solution chemistries or by solid phase chemistries. The chemistries of the two methods are quite similar. Both require a sequence of reactions involving the coupling of a protected amino acid with a peptide chain, deprotecting the newly-coupled amino acid, and with some chemistries, neutralization. Solution chemistry differs from solid phase chemistry primarily in the methods use for isolation and purification of the chemical intermediates. In a solution synthesis, the intermediates are usually isolated by precipitation or evaporation of the solvent. The purifications are done by such techniques as recrystallization, precipitation, and chromatography. On the other hand, in a solid phase synthesis, in which the growing peptide chain is attached to the solid substrate, the isolation is done by filtration, and the purifications are done by washing with solvent and filtration. Because these steps are repetitive, the solid phase method can be automated.

A typical solid phase peptide synthesis is often referred to as the Merrifield Method after its inventor Dr. Bruce Merrifield of Rockefeller University. The Merrifield process starts with an amino acid coupled via the alphacarboxyl group to a suitable resin. The alpha-amino group of the carboxyl terminal amino acid of the peptide being protected by a t-butyloxycarbonyl (BOC) group which reduces the nucleophilicity of the nitrogen. The coupling of each subsequent amino acid incorporates the following reaction scheme:

1. Removal of the BOC group with 50 percent trifluoroacetic acid (TFA) in dichloromethane. This step is often performed in two stages: a short (5 minute) deprotection to condition the resin, and a long (20–30) minute treatment to insure complete removal or deprotection.

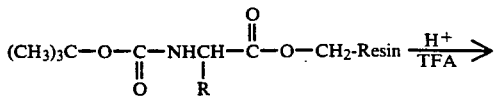

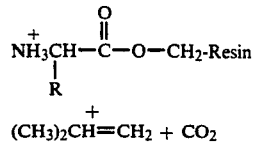

2. Washing the resin with dichloromethane to remove all traces of TFA. This washing step is usually repeated 3 or 4 times.

3. Neutralizing with 5 percent triethylamine (TEA) in dichloromethane in order to deprotonate the alpha-amino terminus resulting from the deprotection step so that the subsequent nucleophilic displacement coupling reaction will proceed. This step is usually performed twice to insure complete neutralization.

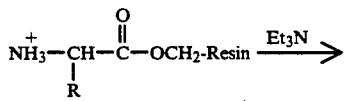

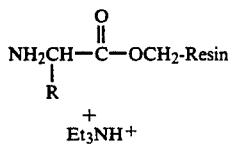

4. Washing the resin with dichloromethane 3 or 4 times to remove excess TEA and TEA salts.

5. a) Adding 3-fold molar excess of a BOC-protected amino acid dissolved in dichloromethane to the reaction mixture followed by an equivalent amount of a carboxyl group activating reagent such as dicyclohexylcarbodiimide (DCC). The coupling reaction is nearly complete in 15 minutes or less but peptide chemists often let the reaction run for an hour or more to insure complete reaction.

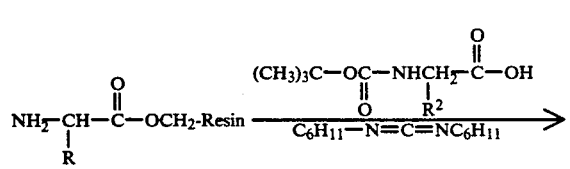

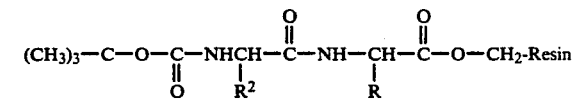

6. Washing the resin ester with dichloromethane 3 or 4 times to remove excess reagents and by-products from the chemical reaction. One by-product, dicyclohexylurea (DCU), is insoluble in dichloromethane and is often removed by washing the system with 3 or 4 volumes of methanol. The methanol washes are followed by 3 or 4 dichloromethane washes to prepare the system for the next cycle.

Even though this coupling method is very effective, it is costly because one equivalent of reagent is wasted for each equivalent that couples. To reduce this waste, some researchers add an alcohol, such as N-hydroxylbenzotriazole, that forms an active ester of the amino acid.

Because this intermediate is unstable and rearranges to a very stable acylurea which consumes active reagents, many scientists modify this reaction scheme.

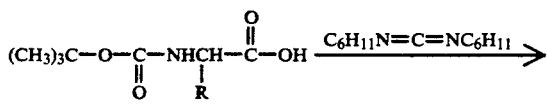

If only one-half equivalent of protected amino acid is used, an active symmetric anhydride is formed.

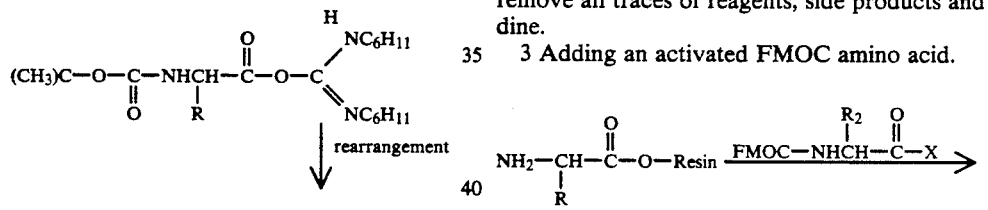

Most automated peptide synthesizers also perform the symmetric anhydride and active ester chemistries automatically. One commercial machine, sold by Applied Biosystems, Inc., does these chemistries in a manner described in U.S. Pat. No. 4,668,476. This on-machine activation is a major portion of the cost of the construction of such machines.

The Merrifield BOC solid phase method depends upon having a C-terminal amino acid resin linkage that is stable to mild acid such as trifluoroacetic acid and unstable to (cleaved by) strong acids such as anhydrous hydrofluoric acid.

An alternative procedure for solid phase synthesis relies on a base-labile protecting group on the alpha-amino group, such as flourenylmethoxycarbonyl (FMOC), instead of the acid-labile BOC group. By using this type of protection, the linkage between the C-terminal amino acid and the resin support can be labile to mild acids like trifluoroacetic acid. This then eliminates the need for using anhydrous hydrofluoric acid at the end of the synthesis.

The general protocol for the addition of one amino acid to the peptide chain using the base labile deprotection scheme is as follows:

1. Removal of the FMOC protecting group with 20 percent piperidine in dimethylformamide (DMF).

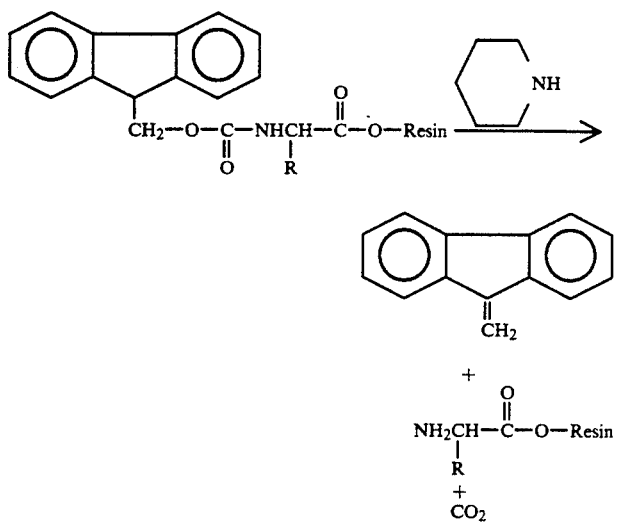

2. Washing the resin with pure DMF 3 or 4 times to remove all traces of reagents, side products and piperidine.

3 Adding an activated FMOC amino acid.

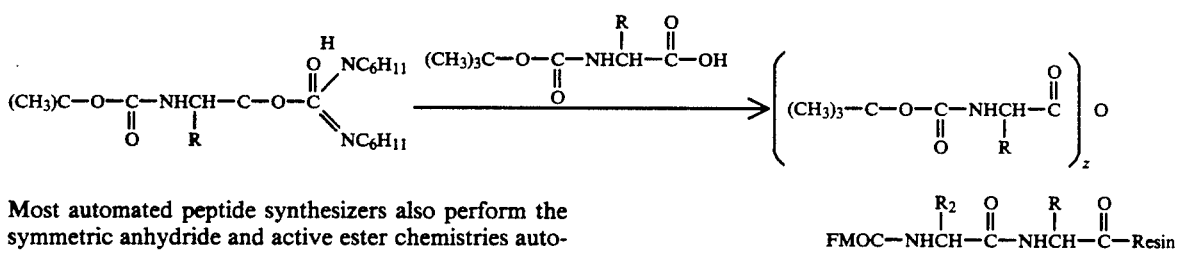

4. Washing the resin 3 or 4 times with pure DMF to remove any excess FMOC amino acid ester and reaction by-products.

5. Repeating this cycle until the desired peptide chain has been constructed.

Even though this procedure is simplified, an activated amino acid is still required as the BOC procedure described above and the same cost factors apply. Preformed activated amino acids (e.g. pentafluorophenyl esters) are stable in dry form but are not as reactive as the symmetric anhydrides described above, thus product yield is lower and reaction times are longer.

An alternative activation method that has many advantages over the DCC methods described above has been used for the base labile FMOC approach by the inventors and others (Fournier, et al.; 1987 Peptide Symposium Proceedings), which utilizes benzotriazole-1-yl-oxy-tris(dimethylamino)phosphonium hexafluorophosphate (BOP or Castro's reagent), as the activating agent instead of DCC:

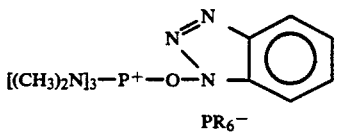

In this method, there are no insoluble by-products formed. The chemical intermediate is more reactive and better coupling yields have been reported. However, because the reagent is not very stable in solution, new reagent must be prepared for the machine each day or two. This prevents long term unattended automated synthesis which reduces the main advantages of an automated peptide synthesizer.

BRIEF DESCRIPTION OF THE INVENTION

It has been unexpectedly discovered in accordance with this invention that a dry mixture of a protected amino acid and its activating agent is stable, and when dissolved in an appropriate reaction solvent, rapidly forms a highly reactive reagent. As a general rule, reactive solid reagents which, when combined, react to form a highly reactive intermediate, are unstable when mixed together as solids. Surprisingly, this has been found not to be true when a protected amino acid, preferably a FMOC-protected amino acid, is mixed with its solid activating agent, preferably BOP.

This invention allows significant improvements in the delivery of reagents required for automated peptide synthesis. It allows users to conveniently use well-proven, highly reactive chemistries while simultaneously reducing the number and complexity of components required for performing the synthesis. The FMOC/BOP premix method of in-vial activation along with other in-vial activation methods drastically reduce the capital costs of automated peptide synthesis. Current state-of-the-art equipment requires in-situ activation of amino acids. In some cases, the cost of components needed to accomplish this represents 50%-70% of the total equipment cost due to the number of additional valves, controls, vessels, reagents, solvents, etc.

According to this invention, dry solid protected amino acids can be packaged and stored with dry solid BOP activating reagent. Thus, quantities of each reagent (protected amino acid and activating reagent) sufficient for a single amino acid coupling can be provided in a single disposable vial. This allows the construction of a much more simplified machine, requiring significantly fewer parts than current technology. Formation of the reactive species is accomplished in the vial upon addition of appropriate solvent just prior to use. Consequently, the need for reagent reservoirs and associated valves, activation vessels and their associated valves, solvent exchange vessels and their associated valves, and all of the other components and their control systems are eliminated. As a result of this invention, not only are instrumentation costs reduced, but operation costs are reduced as well by eliminating reagent waste.

The dry reagent of this invention comprises a predetermined amount of each of a protected amino acid and an activating agent for the protected amino acid. The particular identities of protected amino acids and their activating agents are generally known, and applicant does not claim to have discovered specific protected amino acids or activating agents. As a general rule, there should be at least one mole of activating agent in the dry mixture for each mole of protected amino acid. The ratio of activating agent to amino acid can be as high as 2:1, or even higher, but no particular advantage is achieved with such high amounts. In general, a slight excess of activating agent, e.g., a mole ratio in the range of from about 1:1 to about 1.3:1 is preferred.

Although this invention is, in principle, applicable to any combination of protected amino acid and activating agent, it is used to special advantage when the protected amino acid is one having a base-labile protecting group on the alpha-amino group of an amino acid, and the activating agent is a penta-valent phosphorous compound. Preferred amino acids are FMOC-protected amino acids and the activating agent is BOP.

The precise amounts of protected amino acid and activating agent are not critical. It is desired, however, that they be convenient to handle and consistent with use in automatic peptide synthesizers. Most laboratory scale synthesizers commonly use either 0.5 millimole or 2 millimole of amino acid for each reaction step, while industrial-scale synthesizers use approximately one kilogram of protected amino acid. The amount of activating agent is adjusted to provide the desired molar ratio.

The reagent of this invention is prepared by dry mixing the selected protected amino acid and activating agent by known dry blending techniques. Since these ingredients are anhydrous, the mixing must be under anhydrous conditions. Furthermore, the mixture should be free of any reaction solvent. The resulting mixture is then charged to a vial or other moisture or solvent impermeable container and the container is sealed.

At the time of use, the container is opened, and the reagent is dissolved in an appropriate reaction solvent. In the case of FMOC-protected amino acid and a BOP-activating agent, the solvent typically is a solution of N-methylmorpholine in dimethylforamide. Dissolution is preferably achieved by adding solvent directly to the container. Consequently, the volume of the container should be sufficient to accept the necessary amount of solvent to achieve dissolution of the two reagents and the desired concentration in the solvent. The resulting solution is then mixed with a deprotected solid-phase peptide substrate, such as a Merrifield-type resin, and the coupling reaction is allowed to occur.

The following examples are illustrative:

EXAMPLE I

One millimole of FMOC protected valine was mixed with 1.1 millimoles of BOP reagent in a 12 cc vial compatible with the sample table of a solid phase synthesizer. The stability of the reagent was checked by dissolving the mixture containing 0 10 millimole of the FMOC-valine in 2 ml of a 10% N-methylmorpholine solution in dimethylformamide and doing a coupling reaction on 100 mg (0.056 millimole) of Merrifield valine resin. The extent of the coupling reaction was determined by the standard Kaiser ninhydrin test (Stewart and Young; Solid Phase Peptide Synthesis, Second Edition; Pierce Chem. Co. 1984) and visual inspection of the mixed dry powders. The results of these experiments are summarized in Table I below and show that there was no perceptible decomposition or reduction in coupling efficiency after 8 weeks.

TABLE 1

| Time | Appearance | Coupling Time | Yield |
|------|------------|---------------|-------|
| 0 | White powder | 30 min. | 99.5% |
| 4 wks. | No change | 30 min. | 99.5% |
| 8 wks. | No change | 30 min. | 99.5% |

EXAMPLE II

A 1.398-gram (0.5 mMole) portion of FMOC-leucine-pbenzyloxybenzyl alcohol resin was placed in the reaction vessel of an automated peptide synthesizer. The resin was mixed with 15 ml of dimethylformamide for 1 minute. This solvent wash was performed three times. The FMOC amino acid resin was deprotected by first mixing with 10 ml of 20% piperidine in DMF for 3 minutes and a second time for 10 minutes. Then the resin was washed 6 times with 15 ml of DMF for 1 minute each repitition. A previously prepared dry mixture of FMOC glutamic acid (1.0 mM 369 mg) and benzotriazole-1-yl-oxy-tris (dimethylamino)phosphonium hexafluorophosphate (BOP 1.2 mM, 532 mg) was dissolved in 8.0 ml DMF. 2.0 ml of 10% NMM (N-methyl morpholine) was added. The solution stood for 5 minutes and then was mixed with the resin for 1 hour. The resin was washed 3 times with DMF for 1 minute each time. This procedure was repeated, using a dry pre-mixed FMOC amino acid/BOP activating reagent for each amino acid until the following sequence was complete:

Val-Glu-Glu-Asp-Thr-Lys-Ser-Glu-Lys-Asp-Glu-Leu-Resin

What is claimed is:

1. A dry, pre-mixed and shelf stable two component reagent for solid phase peptide synthesis consisting essentially of a protected amino acid and an activating agent for the protected amino acid for said synthesis, wherein the mole ratio of activating agent to protected amino acid is at least 1:1, said mixture being free of reaction solvent.

2. A reagent according to claim 2, wherein said protected amino acid has a base-labile protecting group, and said activating agent is a pentavalent phosphorous compound.

3. A reagent according to claim 2, wherein said protecting group is the fluorenylmethoxycarbonyl group, and said phosphorous compound is benzotriazole-1-yl-oxytris(dimethylamino)phosphonium hexafluorophosphate.

4. In a method for preparing a synthetic peptide in a solid-phase reaction of a protected amino acid with a deprotected resin-supported peptide chain, the improvement of carrying out said reaction by mixing a preformed, solvent free, shelf stable, two component solid mixture of anhydrous protected amino acid anhydrous activating agent in a molar ratio of activating agent to amino acid of at least about 1:1 with a reaction solvent, and thereafter mixing the resulting solution with said resin-supported peptide chain.

5. A method according to claim 4, wherein said protected amino acid has a base-labile protecting group, and said activating agent is a pentavalent phosphorous compound.

6. A method according to claim 5, wherein said protecting group is the fluorenylmethoxycarbonyl group said phosphorous compound is benzotriazole-1-yl-oxy-tris(dimethylamino)phosphonium hexafluorophosphate.

7. A pre-packaged reagent kit for solid phase peptide synthesis comprising a dry, shelf stable, and pre-mixed two component reagent consisting essentially of a protected amino acid and an activating agent for the protected amino acid for said synthesis, wherein the mole ratio of activating agent to protected amino acid is at least 1:1, said reagent being free of reaction solvent, and a container for said reagent.

8. The pre-packaged reagent kit according to claim 7, wherein said protected amino acid has a base-labile protecting group, and said activating agent is a pentavalent phosphorous compound.

9. The pre-packaged reagent kit according to claim 8, wherein said protecting group is the fluorenylmethoxycarbonyl group, and said phosphorous compound is benzotriazole-1-yl-oxy-tris(dimethylamino)phosphonium hexafluorophosphate.

10. The pre-packaged reagent kit according to claim 7, wherein the container is a disposable vial.

* * * * *